US010220131B2

(12) United States Patent
Kuchiki et al.

(10) Patent No.: US 10,220,131 B2
(45) Date of Patent: Mar. 5, 2019

(54) BLOOD PURIFICATION SYSTEM

(71) Applicant: Nikkiso Company Limited, Tokyo (JP)

(72) Inventors: Masaru Kuchiki, Makinohara (JP);
Hiroaki Suzuki, Makinohara (JP);
Harutoshi Okabe, Makinohara (JP)

(73) Assignee: Nikkiso Company Limited, Tokyo (JP)

( * ) Notice: Subject to any disclaimer, the term of this patent is extended or adjusted under 35 U.S.C. 154(b) by 118 days.

(21) Appl. No.: 14/093,422

(22) Filed: Nov. 30, 2013

(65) Prior Publication Data

US 2014/0110318 A1    Apr. 24, 2014

Related U.S. Application Data

(63) Continuation of application No. PCT/JP2012/064130, filed on May 31, 2012.

(30) Foreign Application Priority Data

Jun. 1, 2011   (JP) .................................. 2011-123392

(51) Int. Cl.
*A61M 1/16* (2006.01)
*A61M 1/14* (2006.01)
*C02F 1/44* (2006.01)
*C02F 103/02* (2006.01)

(52) U.S. Cl.
CPC ............ *A61M 1/1654* (2013.01); *A61M 1/14* (2013.01); *A61M 1/168* (2013.01); *A61M 1/169* (2013.01); *A61M 1/1656* (2013.01); *A61M 1/1686* (2013.01); *A61M 2205/3561* (2013.01); *A61M 2205/3584* (2013.01); *A61M 2205/84* (2013.01); *C02F 1/441* (2013.01); *C02F 2103/026* (2013.01); *F04C 2270/041* (2013.01)

(58) Field of Classification Search
USPC ................................ 210/140, 142, 143, 96.2
See application file for complete search history.

(56) References Cited

U.S. PATENT DOCUMENTS

| | | | |
|---|---|---|---|
| 4,596,549 A | 6/1986 | Minami | |
| 5,015,389 A * | 5/1991 | Portillo, Jr. | ......... A61M 1/1656 210/646 |
| 2008/0312960 A1 | 12/2008 | Nikolic et al. | |

(Continued)

FOREIGN PATENT DOCUMENTS

| | | |
|---|---|---|
| JP | 52-45438 | 11/1977 |
| JP | 6-9668 | 3/1994 |
| JP | 2004-016412 | 1/2004 |

(Continued)

*Primary Examiner* — Dirk R Bass
(74) *Attorney, Agent, or Firm* — Harness, Dickey & Pierce, P.L.C.

(57) ABSTRACT

The blood purification system includes a plurality of monitoring devices (1) with a dialyzer (5) to perform a blood purification treatment on a patient. A dialysate supplying device (2) supplies a dialysate to each of the monitoring devices (1). The plurality of monitoring devices (1) and the dialysate supplying device (2) are connected to each other by a LAN cable α. Predetermined information can be transmitted from the dialysate supplying device (2) to a specified monitoring device (1), out of the plurality of monitoring devices (1). The specified monitoring device (1) can perform an individual operation.

11 Claims, 6 Drawing Sheets

(56) References Cited

U.S. PATENT DOCUMENTS

2010/0181235 A1 7/2010 Fava et al.
2012/0175296 A1* 7/2012 Wehmeyer .......... A61M 1/1654
 210/321.69

FOREIGN PATENT DOCUMENTS

| JP | 2008-023324 | 2/2008 |
| JP | 2008-220784 | 9/2008 |
| JP | 4536143 | 9/2010 |

* cited by examiner

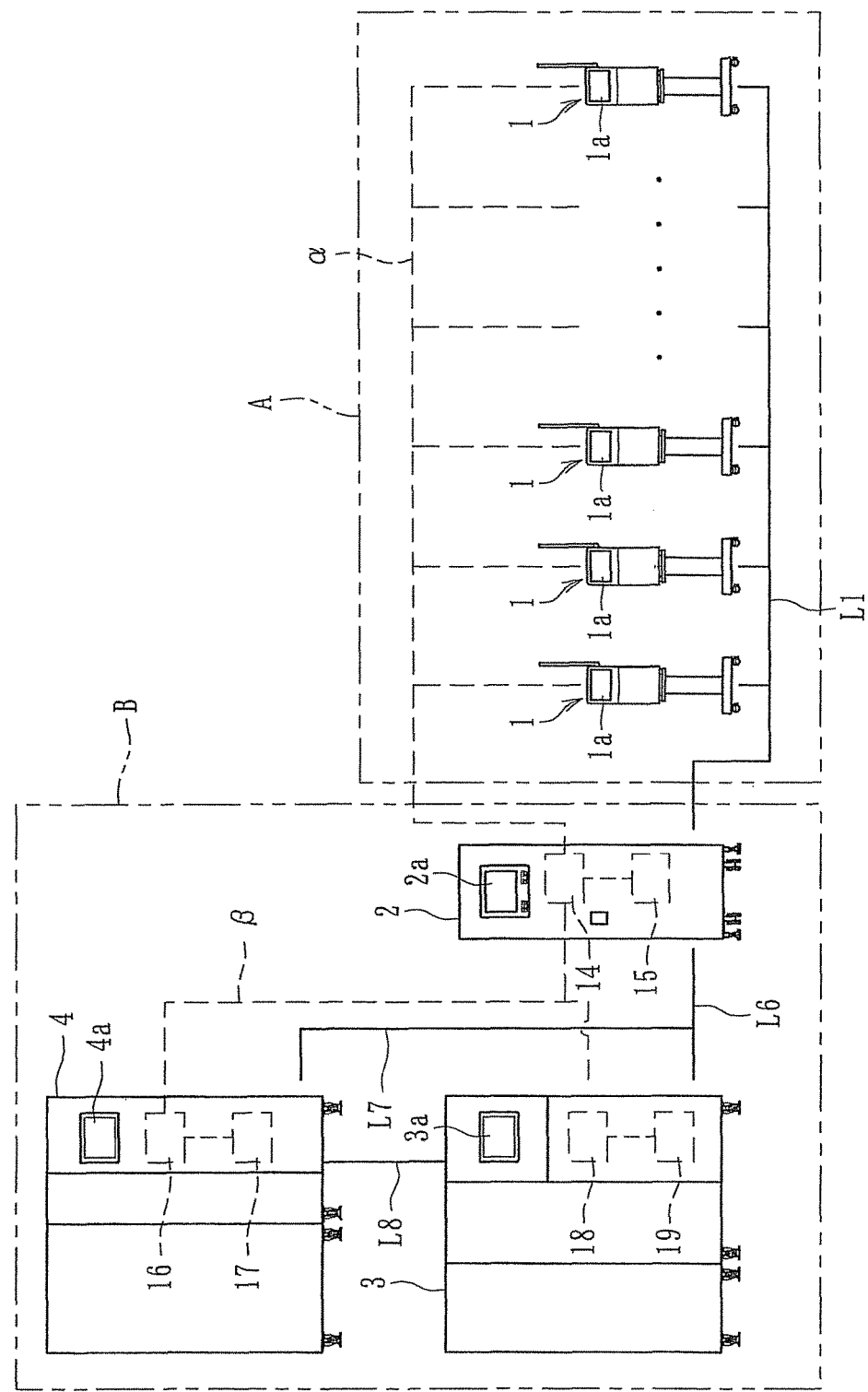
[Fig 1]

[Fig 2]
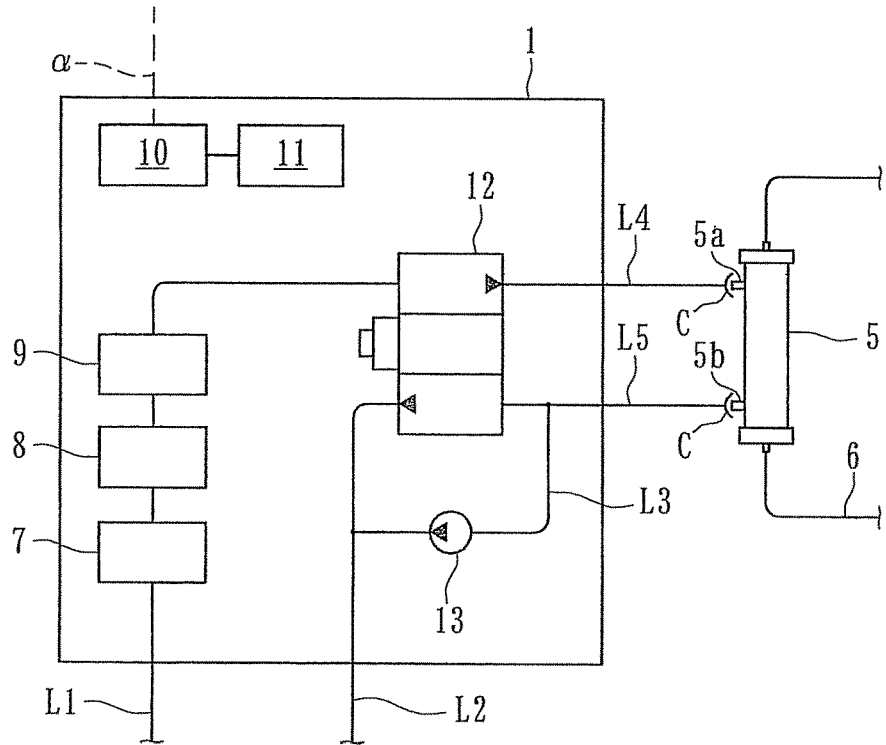
[Fig 3]
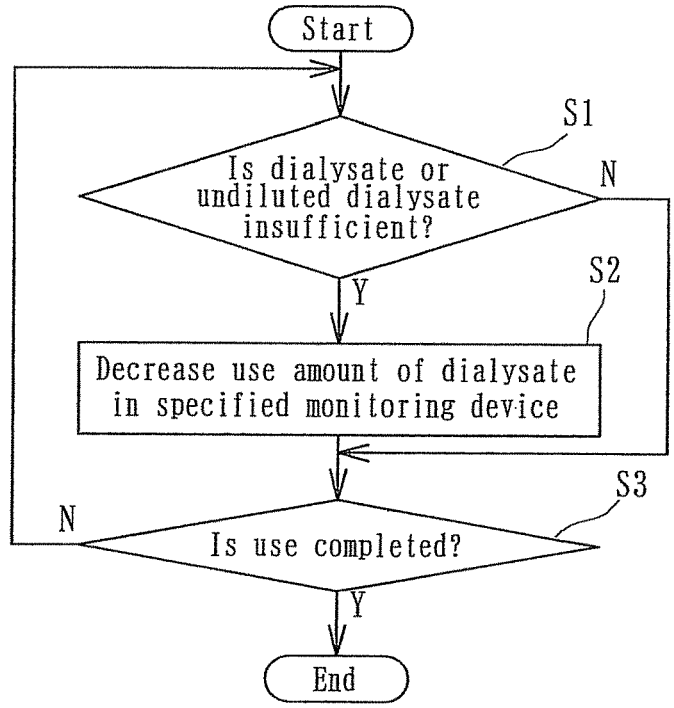

[Fig 4]
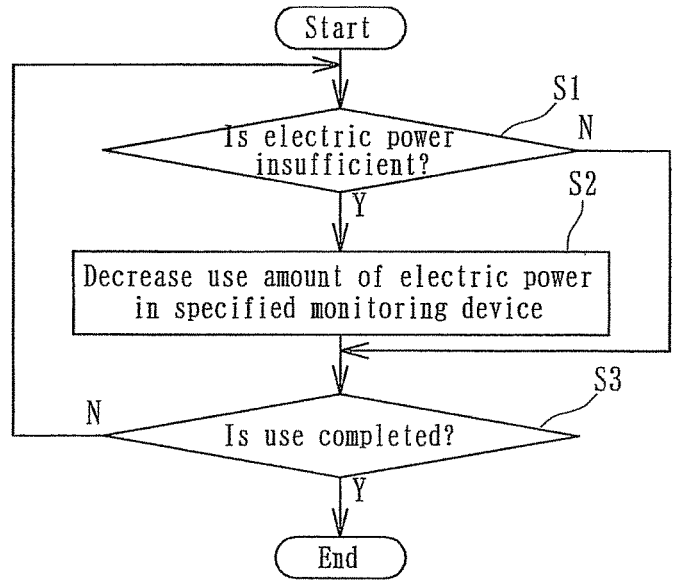
[Fig 5]
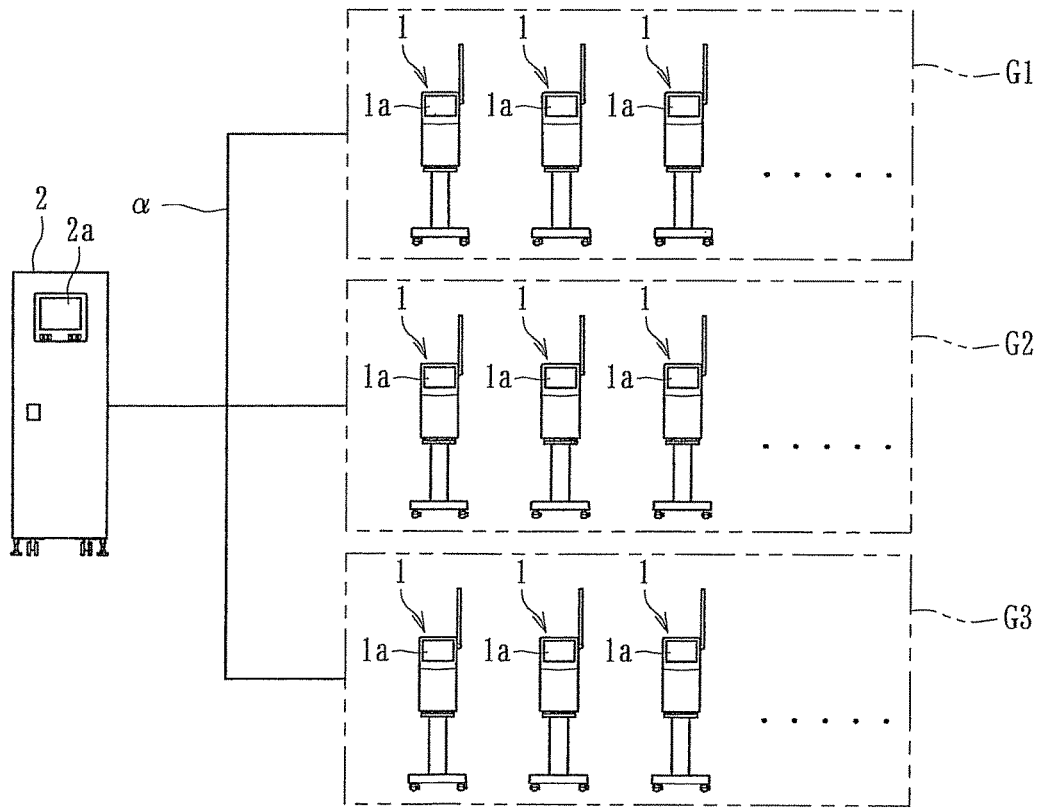

[ Fig 6 ]
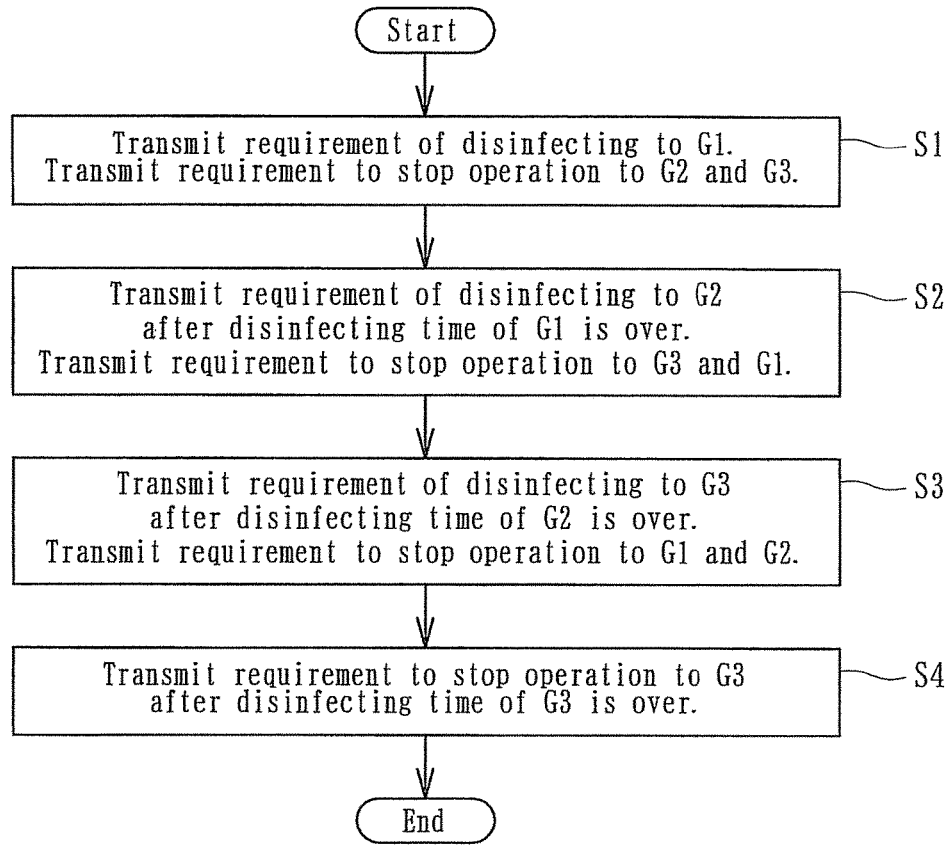
[ Fig 7 ]
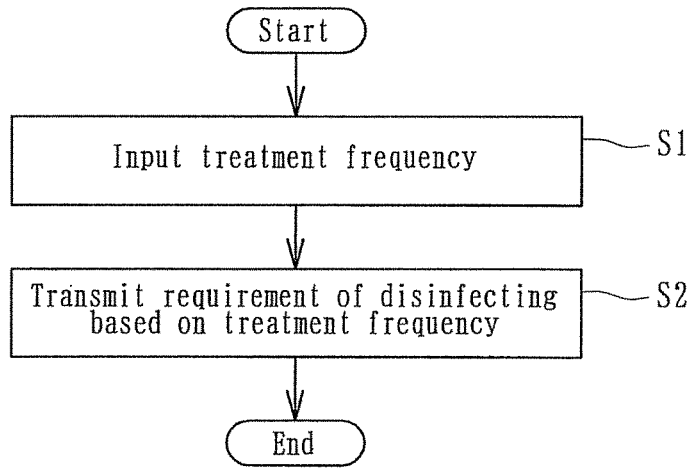

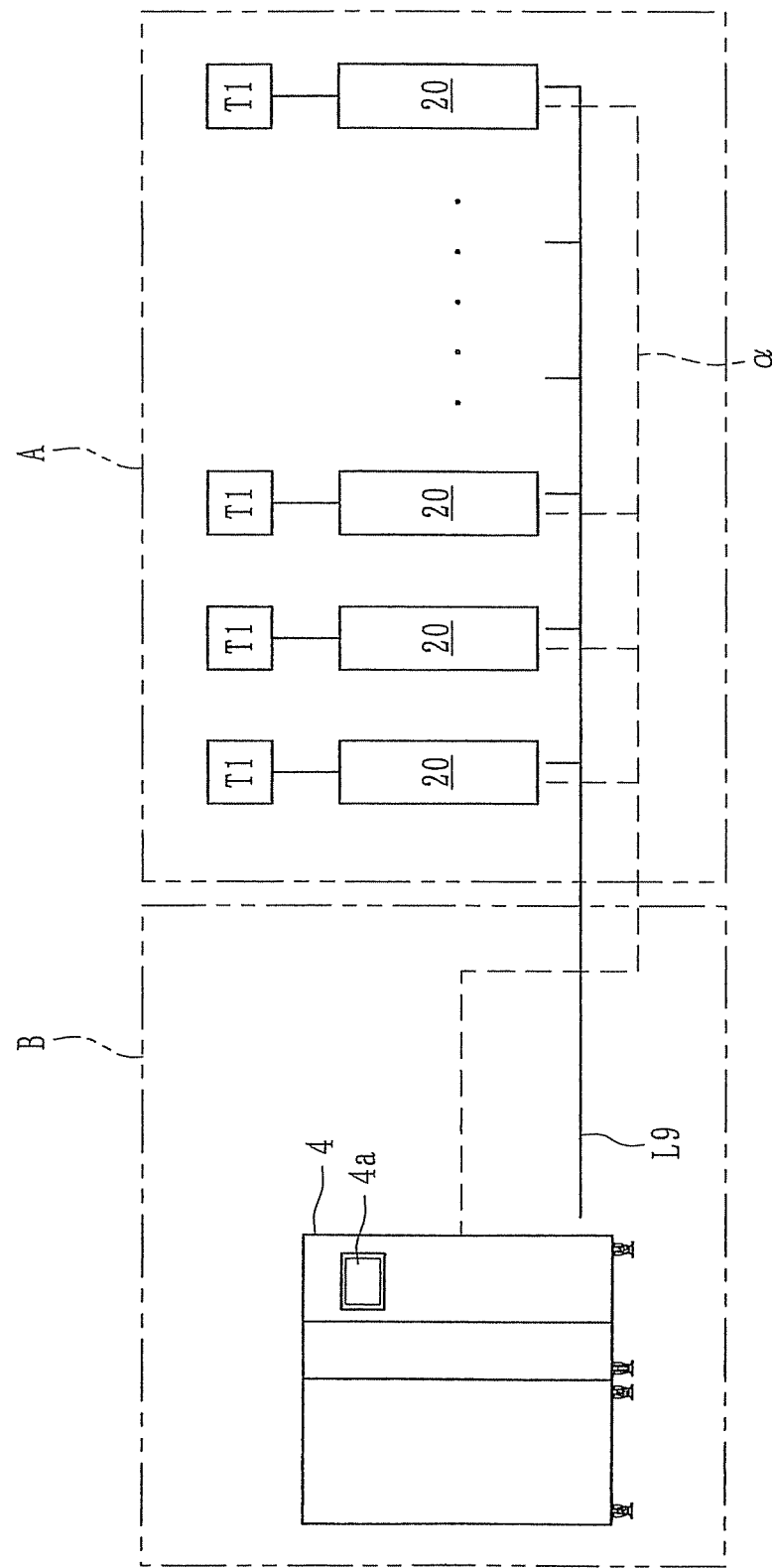

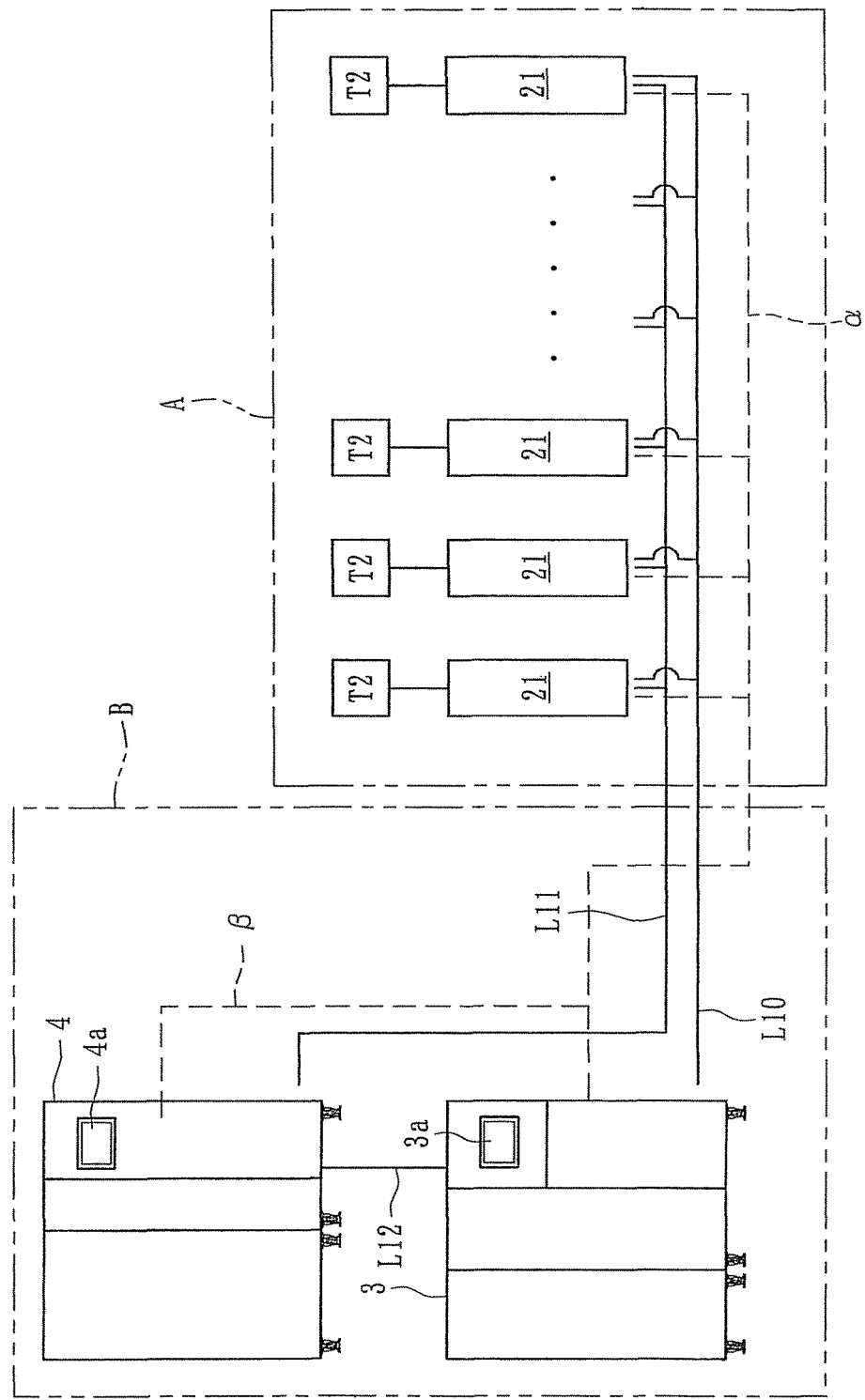

BLOOD PURIFICATION SYSTEM

CROSS-REFERENCE TO RELATED APPLICATIONS

This application is a continuation of International Application No. PCT/JP2012/064130, filed May 31, 2012, which claims priority to Japanese Application No. 2011-123392, filed Jun. 1, 2011. The disclosures of the above applications are incorporating herein by reference.

FIELD

The present disclosure relates to a blood purification system that includes multiple blood purification mechanisms that are attached to blood purifiers to perform a blood purification treatment on patients and a supplying mechanism supplying a dialysate or an undiluted dialysate to each of the blood purification mechanisms.

BACKGROUND

In general, a blood purification system includes a dialysate supplying device that is installed in a machine room in a medical field such as a hospital. A dialysis monitoring device is installed in a separately arranged dialysis room (treatment room). The dialysate supplying device and the dialysis monitoring device are connected to each other by a pipe. The dialysate supplying device produces a dialysate with a predetermined concentration by using supplied clean water. A plurality of dialysis monitoring devices is installed corresponding to the number of blood purifiers (dialyzers) to perform dialysis treatment on patients, introduce the dialysate produced by the dialysate supplying device through the pipe, and supply the dialysate to the blood purifiers.

The dialysate is distributed and fed from the dialysate supplying device, installed in the machine room, to the plurality of dialysis monitoring devices, installed in the dialysis room. The dialysate is supplied to the dialyzers in each dialysis monitoring device. A blood purification system that distributes the dialysate produced in the machine room, as described above, to each dialysis monitoring device, is generally referred to as a "central system for a dialysis treatment". A device that produces the dialysate for each of the blood purifiers (that is, each dialysis treatment patient) is generally referred to as a "personal dialysis device".

In the related art, a technique has been suggested where the dialysate supplying device and each of the dialysis monitoring devices are electrically connected to each other. During a dialysis treatment process, a pipe cleaning process or a pipe disinfecting process, an electrical signal (process signal) is transmitted from the dialysate supplying device (supplying mechanism) to each of the dialysis monitoring devices (blood purification mechanisms). Each of the dialysis monitoring devices, upon receiving a predetermined electrical signal (process signal), performs an operation (driving of a pump or opening and closing of an electromagnetic valve) corresponding to the signal. See, Japanese Unexamined Patent Application Publication No. 2004-16412.

SUMMARY

However, in the related art above-described blood purification system, the electrical signal is transmitted from the dialysate supplying device (supplying mechanism) to each of the dialysis monitoring devices (blood purification mechanism) to perform a uniform operation. Thus, a problem exists in that it is difficult to perform an individual operation depending on various situations on the dialysis monitoring devices. Similarly, such a problem also arises when the blood purification mechanism is adapted to the personal dialysis device.

The present disclosure aims to provide a blood purification system that performs an individual operation depending on various situations in the blood purification mechanisms.

A blood purification system includes multiple blood purification mechanisms attached to blood purifiers to perform a blood purification treatment on a patient. A supplying mechanism is capable of supplying a dialysate, an undiluted dialysate, clean water or an antiseptic solution to each of the blood purification mechanisms. Predetermined information is transmitted from the supplying mechanism to specified blood purification mechanism out of the multiple blood purification mechanisms. The specified blood purification mechanism can perform an individual operation.

In the blood purification system, depending on the status of the supplying mechanism, the specified blood purification mechanism is operated or stopped, or a drive amount of an actuator provided in the specified blood purification mechanism is decreased.

The supplying mechanism includes a dialysate supplying device that produces a dialysate with a predetermined concentration by using clean water and an undiluted dialysate. The blood purification mechanisms include a monitoring device that supplies the dialysate supplied from the dialysate supplying device to the blood purifier.

The supplying mechanism includes a water treatment device that produces clean water. The blood purification mechanisms include a personal dialysis device that produces a dialysate with a predetermined concentration by using the clean water supplied from the water treatment device. The personal dialysis device supplies the dialysate to the blood purifier.

The supplying mechanism includes a water treatment device and a dissolving device. The water treatment device produces clean water. The dissolving device produces an undiluted dialysate with a predetermined concentration, by using the clean water produced in the water treatment device. The blood purification mechanism includes a personal dialysis device that produces a dialysate with a predetermined concentration by using the undiluted dialysate and the clean water. The undiluted dialysate and clean water are, respectively, supplied from the dissolving device and the water treatment device. The blood purification mechanism supplies the dialysate to the blood purifier.

In a condition where it is determined insufficient dialysate is supplied from the supplying mechanism or insufficient undiluted dialysate is supplied to the supplying mechanism, an use amount of the dialysate in the specified blood purification mechanism is decreased.

In a condition where it is determined that insufficient electric power is supplied to multiple blood purification mechanisms, an use amount of the electric power in the specified blood purification mechanism is decreased.

The specified blood purification mechanism includes a predetermined number of blood purification mechanisms that is divided into a group out of multiple blood purification mechanisms.

The disinfecting is sequentially performed for each group by supplying the antiseptic solution from the supplying mechanism to the specified blood purification mechanism that is divided into the group.

The specified blood purification mechanism can be divided into a group for every one frequency of each blood purification treatment. It can be set to have disinfecting time according to an use frequency of the group.

The supplying mechanism and the blood purification mechanism can bilaterally communicate with each other.

The predetermined information can be transmitted from the supplying mechanism to the specified blood purification mechanism out of multiple blood purification mechanism. The specified blood purification mechanism performs the individual operation. Therefore, depending on the various situations, the blood purification mechanism performs the individual operation.

Depending on the status of the supplying mechanism, the specified blood purification mechanism is operated or stopped, or the drive amount of the actuator provided in the specified blood purification mechanism is decreased. Therefore, it is possible for the blood purification mechanism to perform a more appropriate action depending on the various situations of the supplying mechanism.

The supplying mechanism includes a dialysate supplying device that produces a dialysate with a predetermined concentration by using clean water and an undiluted dialysate. The blood purification mechanism includes a monitoring device that supplies the dialysate, supplied from the dialysate supplying device, to the blood purifier. Therefore, the blood purification system can be applied to a central system.

The supplying mechanism includes the water treatment device that produces clean water. The blood purification mechanism includes the personal dialysis device that produces the dialysate, with predetermined concentration by using the clean water supplied from the water treatment device, and supplies the dialysate to the blood purifier. Therefore, the blood purification system can be applied to a blood purification system having personal dialysis devices.

The supplying mechanism includes the water treatment device and the dissolving device. The water treatment device produces clean water. The dissolving device produces the undiluted dialysate with a predetermined concentration by using the clean water produced in the water treatment device. The blood purification mechanism includes the personal dialysis device. The personal dialysis device produces the dialysate with a predetermined concentration by using the undiluted dialysate and the clean water. The undiluted dialysate and clean water are, respectively, supplied from the dissolving device and the water treatment device. The personal dialysis device supplies the dialysate to the blood purifier. Therefore, the blood purification system can be applied to a blood purification system with the personal dialysis device.

In a condition where it is determined that insufficient dialysate is supplied from the supplying mechanism or insufficient undiluted dialysate is supplied to the supplying mechanism, the use amount of the dialysate in the specified blood purification mechanism is decreased. Therefore, it is possible for the blood purification mechanism to perform an individual action according to the dialysate or the undiluted dialysate.

In a condition where it is determined that insufficient electric power is supplied to multiple blood purification mechanism, the use amount of the electric power in the specified blood purification mechanism is decreased. Therefore, it is possible for the blood purification mechanism to perform an individual action according to the electric power supply.

The specified blood purification mechanism includes the predetermined number of blood purification mechanism divided into a group out of multiple blood purification mechanism. Therefore, it is possible for the blood purification mechanism to easily perform an individual operation depending on the various situations.

The disinfecting is sequentially performed on each group by supplying the antiseptic solution from the supplying mechanism to the specified blood purification mechanism that are divided into the group. Therefore, more efficient disinfecting can be performed.

The specified blood purification mechanism can be divided into a group for every one frequency of each blood purification treatment. The blood purification mechanism can be set to have disinfecting time according to a use frequency of the group. Therefore, more efficient disinfecting can be performed according to the use frequency.

The supplying mechanism and the blood purification mechanism can bilaterally communicate with each other. Therefore, various items of information can be communicated between the supplying mechanism and the blood purification mechanisms. It is possible to perform a more appropriate and operable blood purification treatment.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is an overall schematic view of a blood purification system according to an embodiment of the present disclosure.

FIG. 2 is a schematic view of a configuration of a monitoring device in the blood purification system.

FIG. 3 is a flowchart illustrating control content, when dialysate or undiluted dialysate is insufficient, of a dialysate supplying device in the blood purification system.

FIG. 4 is a flowchart illustrating control content, when electric power is insufficient, of the dialysate supplying device in the blood purification system.

FIG. 5 is a schematic view illustrating divided groups in the blood purification system.

FIG. 6 is a flowchart illustrating control content of sequential disinfecting of the dialysate supplying device in the blood purification system.

FIG. 7 is a flowchart illustrating control content, of disinfecting according to a frequency of treatment, of the dialysate supplying device in the blood purification system.

FIG. 8 is an overall schematic view of a blood purification system according to another embodiment.

FIG. 9 is an overall schematic view of a blood purification system according to still another embodiment.

DETAILED DESCRIPTION

An embodiment of the present disclosure will be described in detail with reference to the drawings.

A blood purification system according to the present embodiment produces a dialysate with a predetermined concentration using an undiluted dialysate. The system supplies the dialysate to a plurality of dialysis monitoring devices. As illustrated in FIG. 1, the blood purification system is mainly configured to include a plurality of monitoring devices 1. The monitoring devices 1 are installed in a dialysis room A (treatment room) in a medical field, such as a hospital. A dialysate supplying device 2, a dissolving device 3 and a water treatment device 4 are installed in a machine room B. The machine room is a place separated from the dialysis room A in the medical field.

The monitoring device 1 (blood purification mechanism) includes a dialyzer 5 (blood purifier) that performs a blood purification treatment (hemodialysis treatment) on a patient. The monitoring device 1 supplies the dialysate supplied from the dialysate supplying device 2 to the dialyzer 5. A plurality of monitoring devices 1 is installed at the dialysis room A. The monitoring devices 1 include touch panels is that display instructions and predetermined hemodialysis treatments or other control content (cleaning or disinfecting).

More specifically, as illustrated in FIG. 2, a pipe L1 extends from the dialysate supplying device 2. The pipe L1 is drawn into each of the plurality of monitoring devices 1 installed at the dialysis room A. A pipe L2 is connected to a liquid discharge device (not illustrated). A duplex pump 12 is arranged across the pipes L1 and L2. A flow rate detection sensor 7, a liquid pressure detection sensor 8, and conductive detection sensor 9 are positioned out of the pipes L1 and L2 and in the pipe L1 inside the monitoring device 1. The flow rate detection sensor 7 detects a flow rate of a liquid flowing in the pipe L1. The liquid pressure detection sensor 8 detects a liquid supply pressure of the liquid. The conductivity detection sensor 9 detects conductivity (concentration) of the liquid.

In addition, a dialysate introduction line L4, communicating with the pipe L1, and a dialysate discharge line L5, communicating with the pipe L2, extended from the duplex pump 12. A tip of the dialysate introduction line L4 can be connected to a dialysate introduction port 5a of the dialyzer 5, via a coupler C. A tip of the dialysate discharge line L5 can be connected to a dialysate discharge port 5b of the dialyzer 5, via the coupler C. In this manner, the dialyzer 5, depending on each patient, is attached to each monitoring device 1. A blood circuit 6, that extracorporeally circulates blood of the patient, is connected to the dialyzer 5.

A pump room of the duplex pump 12 is divided into a liquid supply side pump room, connected to the pipe L1, and a discharge side pump room, connected to the pipe L2 by a single plunger (not illustrated). The plunger performs reciprocation in the pump room. Thus, it supplies the dialysate or a cleaning solution to the liquid supply side pump room to the dialyzer 5. The dialysate inside the dialyzer 5 is sucked into the discharge side pump room. Further, a pipe L3, which bypasses the duplex pump 12, communicates with the pipe L2 and the dialysate discharge line L5. The pipe L3 is formed inside the monitoring device 1. A water removal pump 13 is arranged in the middle of the pipe L3. It is possible to perform water removal on the blood of a patient, which flows inside the dialyzer 5, by driving the water removal pump 13.

Instead of the duplex pump 12, a so-called chamber type may be used. Also, the flow rate detection sensor 7, the liquid pressure detection sensor 8 or the conductivity detection sensors 9 arranged in pipe L1, may be substituted by any sensor, or other generic sensors may be added to pipe L1. Further, in the present embodiment, the sensors are arranged in the pipe L1. However, the sensors may be arranged in the other pipe (for example, the pipe L2). For example, the flow rate detection sensor 7, the liquid pressure detection sensor 8 or the conductivity detection sensor 9 may be arranged in either pipe L1 and pipe L2, or they may be arranged in both pipes.

The water treatment device 4 includes a module (purifying filter) having an inherent filtration membrane. The water treatment device 4 obtains clean water (RO water) by purifying raw water. The water treatment device 4 supplies the clean water to the dissolving device 3. The water treatment device 4 is connected to the dissolving device 3, via a pipe L8. The water treatment device 4 supplies the clean water to the dialysate supplying device 2, via pipes L6 and L7. The clean water obtained by the water treatment device 4 is used when the dialysate supplying device 2 produces the dialysate. Additionally, the clean water is used as the cleaning water for cleaning the pipes of the dialysate supplying device 2 or the monitoring devices 1. Additionally, the water treatment device 4 is connected to supply the clean water to a personal dialysis device (not illustrated) or a dissolving device that dissolves a powdered dialysis drug.

In addition, the water treatment device 4 includes a touch panel 4a, an interface unit 16 and a control unit 17. The touch panel 4a can perform an instruction and display predetermined control content relating to the water treatment. The interface unit 16 is electrically connected to a LAN cable β. If the interface unit 16 receives predetermined information from the dialysate supplying device 2, a predetermined operation (producing the clean water) is performed by the control unit 17 based on the information.

A predetermined amount of powder drug, for dialysis, is dispensed to the dissolving device 3. The dissolving devices mix the powder drug, for dialysis, with the clean water supplied from the water treatment device 4. This produces the undiluted dialysate with a predetermined concentration. The dissolving device 3 includes a touch panel 3a, interface unit 18 and a control unit 19. The touch panel 3a can perform an instruction and display predetermined control content relating to the producing of the undiluted dialysate. The interface unit 18 is electrically connected to a LAN cable β (to be described later). If the interface unit 18 receives predetermined information from the dialysate supplying device 2, a predetermined operation (producing the undiluted dialysate) is performed by the control unit 19 based on the information. The dissolving device 3 is connected to the dialysate supplying device 2 via the pipe L6. The dissolving device 3 supplies the produced undiluted dialysate to the dialysate supplying device 2.

The dialysate supplying device 2, the dissolving device 3 and the water treatment device 4 are connected to each other on a local area network (LAN). This enables bilateral information communication. The LAN is not limited to use of the LAN cable β (wired LAN) as in the present embodiment. It may be any one that enables the bilateral information communication in a wireless manner (wireless LAN). Instead of the LAN, a system may be used that transmits an electrical signal (process signal) unilaterally from the dialysate supplying device 2 to the dissolving device 3 and the water treatment device 4.

The dialysate supplying device 2 (supplying mechanism) can produce the dialysate with a predetermined concentration by using the clean water obtained from the water treatment device 4 and the undiluted dialysate produced by the dissolving device 3. The dialysate supplying device 2 supplies the produced dialysate to each of the monitoring devices 1 (blood purification mechanism). The dialysate supplying device 2 is connected to each of the plurality of monitoring devices 1 via the pipe L1. The dialysate supplying device 2 supplies a desired liquid such as the dialysate, the cleaning water and the antiseptic solution to each of the monitoring devices 1, via the pipe L1. The dialysate supplying device 2 includes a touch panel 2a that performs an instruction and a display predetermined control content relating to the supplying of the dialysate, the cleaning or the disinfecting.

In the blood purification system according to the present embodiment, the dialysate supplying device 2 (supplying mechanism) and each of the monitoring devices 1 (purification device) are connected to each other on the local area network (LAN). Thus, this enables the bilateral information communication. In this configuration of the blood purification system, the predetermined information can be transmitted from the dialysate supplying device 2 out to the specified monitoring device 1 of the plurality of monitoring devices 1. The specified monitoring device 1 can perform the individual operation.

The LAN connection is made via the LAN cable a between the dialysate supplying device 2 and each of the monitoring devices 1. The dialysate supplying device 2 includes the interface unit 14 and the control unit 15 in order to communicate with the monitoring devices 1, via the LAN cable α. Each monitoring device 1 includes the interface unit 10 and the control unit 11 (refer to FIG. 2) in order to communicate with the dialysate supplying device 2 via the LAN cable α. The LAN is not limited to use of the LAN cable α (wired LAN) as in the present embodiment. A connection may be used that enables wireless bilateral information communication (wireless LAN).

If the interface unit 14, of the dialysate supplying device, receives the predetermined information from the monitoring devices 1, the predetermined operation (producing the dialysate) is performed by the control unit 15 based on the information. The predetermined information can be transmitted to the monitoring devices 1 via the interface unit 14. In addition, in the monitoring devices 1, if the interface unit 10 receives the predetermined information from the dialysate supplying device 2, the predetermined operation, such as priming before treatment, hemodialysis treatment, re-transfusion, cleaning and disinfecting, is performed by the control unit 11 based on the information. The predetermined information can be transmitted to the dialysate supplying device 2 via the interface unit 10.

The predetermined information to be transmitted from the dialysate supplying device 2 out to the specified monitoring device 1, of the plurality of monitoring devices 1, is adapted to include information that recognizes situations different from a normal state, for example, suppliable dialysate and undiluted dialysate or insufficient electric power. In particular, depending on the situation, e.g., suppliable amounts of dialysate and undiluted dialysate or electric power, of the dialysate supplying device 2, the specified monitoring device 1 is operated or stopped. Also, the drive amount of the actuator, duplex pump 12 or water removal pump 13, provided in the specified monitoring device 1 is decreased. This selectively decreases the flow rate of the liquid circulating in the pipe L1 or L2. In this manner, it is possible to perform a more appropriate action by operating or stopping the specified monitoring device 1 or by decreasing the drive amount of the actuator provided in the specified monitoring device 1 depending on the situations of the dialysate supplying device 2.

In a condition where it is determined that insufficient dialysate, supplied from the dialysate supplying device 2, or insufficient undiluted dialysate, supplied to the dialysate supplying device 2, by way of the communication among the dissolving device 3, the water treatment device 4 and each of the monitoring devices 1, the drive amount of the duplex pump 12 in the specified monitoring device 1 can be decreased. This decreases the use amount of the dialysate. In the condition where insufficient dialysate, supplied from the dialysate supplying device 2, or insufficient undiluted dialysate, supplied to the dialysate supplying device 2, is determined, the use amount of the dialysate in the specified monitoring device 1 is decreased. Therefore, it is possible to perform an individual action according to the dialysate or the undiluted dialysate.

In the condition where insufficient dialysate, supplied from the dialysate supplying device 2, or insufficient undiluted dialysate, supplied to the dialysate supplying device 2, is determined, the use amount of the dialysate in the specified monitoring device 1 is configured to be decreased.

The control content in the dialysate supplying device 2, in this case, will be described with reference to the flowchart in FIG. 3. By way of the communication among the dissolving device 3, the water treatment device 4 and each of the monitoring devices 1 communicate with each other to compare the dialysate to be used with the dialysate or the undiluted dialysate, each of which has been produced or can be produced. It is determined whether or not the dialysate or the undiluted dialysate is insufficient (S1). If it is determined that the dialysate or the undiluted dialysate is insufficient, the step proceeds to S2. The predetermined information (drive control information of the duplex pump 12) is transmitted to the specified monitoring device 1. In this case, the monitoring device 1, performing the dialysis treatment on a patient, can decrease the to be supplied dialysate. The drive amount of the duplex pump 12 of the monitoring device 1 for the patient that can decrease the use of the dialysate is decreased. This leads to the decreased use amount of the dialysate of all the monitoring devices 1. In S1, when it is determined that the dialysate or the undiluted dialysate is sufficient, a process in S3 is performed by skipping S2.

Thereafter, it is determined whether or not the use of the dialysate (hemodialysis treatment) is completed (S3). If it is determined that the use of the dialysate is completed, a series of controls is completed. In contrast, if it is determined that the use of the dialysate is not completed, the step returns to S1. It is again determined that the dialysate or the undiluted dialysate is insufficient. In the present embodiment, if it is determined that the dialysate or the undiluted dialysate is insufficient, the drive amount of the duplex pump 12 of the specified monitoring device 1 is decreased. However, as long as the use amount of the dialysate can be decreased, other configurations may be adopted. In a case where a valve is provided that can control an individual liquid supply amount for each of the monitoring devices 1, the use amount of the dialysate is configured to be decreased by the control of the valve.

Further, for example, when the power supply is switched to a private power generation, due to a power failure in the medical facilities, under a condition where the electric power supplied to the monitoring devices 1 is determined to be insufficient, it is possible to decrease the use amount of the electric power in the specified monitoring device 1. In this case, where the electric power to be supplied to the plurality of monitoring devices 1 is determined to be insufficient, the electric power for the dialysate in the specified monitoring device 1 is decreased. Therefore, it is possible to perform an individual action according to the power supply.

In a condition where the electric power to be supplied to the monitoring devices 1 is determined to be insufficient, the use amount of the dialysate in the specified monitoring device 1 is decreased. The control content in the dialysate supplying device 2, in this case, will be described with reference to the flowchart in FIG. 4.

When a decrease in the power supply to the blood purification system is detected, it is determined whether or not the electric power supplied to the monitoring devices 1 is insufficient (S1). If it is determined that the electric power is insufficient, the step proceeds to S2. The predetermined information, drive control information of the duplex pump 12, is transmitted to the specified monitoring device 1. In this case, the monitoring device 1 that performs a dialysis treatment on a patient can decrease the dialysate to be supplied. The drive amount of the duplex pump 12 of the monitoring device 1 in the patient, that can decrease the use of the dialysate, is decreased. This leads to a decrease in the use amount of the electric power for all the monitoring devices 1. In S1, when it is determined that the electric power is sufficient, a process in S3 is performed by skipping S2.

It determined whether or not the use of the dialysate (hemodialysis treatment) is completed (S3). If it is determined that the use of the dialysate is completed, a series of controls is completed. In contrast, if it is determined that the use of the dialysate is not completed, the step returns to S1. Here, it is again determined that the electric power is insufficient. In the present embodiment, if it is determined that the electric power is insufficient, the drive amount of the duplex pump 12 in the specified monitoring device 1 is decreased. However, as long as the electric power to be used can be decreased, other configurations may be adopted. Thus, the power supply is decreased to other configuring elements, such as a heating device, in each of the monitoring devices 1.

For example, in S2, the predetermined information, operation control information of a heater, is transmitted to the specified monitoring device 1. In this case, the monitoring device 1 can decrease the electric power to be supplied to the heater, such as the heating device. This enables a decrease in the use amount of the electric power. In general, when cleaning and disinfecting processes are switched to a substitution process, process where the liquid inside the pipe is substituted with the dialysate instead of the cleaning water or the antiseptic solution, or when the power supply is restored after the power failure, the heaters in all the monitoring devices 1 are simultaneously operated. Accordingly, power consumption is excessively increased for the time being. However, it is possible to suppress a peak of the power consumption by decreasing the operation of the heater in the specified monitoring device 1.

Furthermore, as illustrated in FIG. 5, the specified monitoring device 1 may include a predetermined number of monitoring devices 1 that are divided into groups G1 to G3 out of the plurality of monitoring devices 1. Thus, the predetermined information can be transmitted from the dialysate supplying device 2 to the specified monitoring device 1 belonging to the predetermined groups (G1 to G3) out of the plurality of monitoring devices 1. The specified monitoring device 1 of each group can perform an individual operation. In this manner, if the specified monitoring device 1 includes the predetermined number of monitoring devices 1 that are divided into groups out of the plurality of monitoring devices 1, it is possible to more easily cause the monitoring devices 1 to perform the individual operation depending on various situations.

For example, as illustrated in FIG. 5, the respective monitoring devices 1 are divided into the groups G1 to G3. The disinfecting can be sequentially performed on each group by supplying the antiseptic solution from the dialysate supplying device 2 to the specified monitoring device 1 that is divided into a group. In this case, the disinfecting is sequentially performed on each group by supplying the antiseptic solution from the dialysate supplying device 2 to the specified monitoring device 1 that is divided into the group. Therefore, it is possible to more efficiently perform the disinfecting. Hereinafter, the control content in the dialysate supplying device 2, in this case, will be described with reference to the flowchart in FIG. 6.

First, a requirement is transmitted from the dialysate supplying device 2 to the specified monitoring device 1 belonging to G1. The disinfecting is performed on the monitoring device 1 of G1. A requirement to stop an operation is transmitted to the monitoring devices 1 belonging to the other groups (G2 and G3) (S1). In a condition where disinfecting time is over for the monitoring device 1 belonging to G1, the disinfecting requirement is transmitted from the dialysate supplying device 2 to the specified monitoring device 1 belonging to G2. The disinfecting is performed on the monitoring device 1 belonging to G2. The requirement to stop the operation is transmitted to the monitoring device 1 belonging to the other groups (G1 and G3) (S2).

Subsequently, in a condition where the disinfecting time is over for the monitoring device 1 belonging to G2, the disinfecting requirement is transmitted from the dialysate supplying device 2 to the specified monitoring device 1 belonging to G3. The disinfecting is performed on the monitoring device 1 belonging to G3. The requirement to stop the operation is transmitted to the monitoring devices 1 belonging to the other groups (G1 and G2) (S3). Then, in a condition where the disinfecting time is over for the monitoring device 1 belonging to G3, the requirement to stop the operation is transmitted from the dialysate supplying device 2 to the monitoring device 1 belonging to G3 (S4).

In this manner, a series of controls during the disinfecting is completed. By completing the above-described controls and sequentially performing the disinfecting on the monitoring device 1 of each group, it is possible to efficiently perform the disinfecting. In particular, when the inside of the pipe is sterilized by using hot antiseptic solution or hot water as the antiseptic solution, the disinfecting is performed by concentrating on the monitoring device 1 that is divided into each group. Accordingly, it is possible to suppress a decrease in a temperature of the antiseptic solution, and it is possible to more efficiently perform the disinfecting.

For example, as illustrated in FIG. 5, the respective monitoring devices 1 can be divided into the groups G1 to G3 according to the frequency of the hemodialysis treatments. The disinfecting time can be set according to the use frequency of the group. In this case, the specified monitoring device 1 can be divided into a group for each frequency of the respective hemodialysis treatments (blood purification treatment). The disinfecting time can be set according to the use frequency of the group. Accordingly, it is possible to more efficiently perform the disinfecting according to the use frequency. The control content in the dialysate supplying device 2, in this case, will be described with reference to the flowchart in FIG. 7.

For example, a treatment frequency of the monitoring device 1 is input to the dialysate supplying device 2 in advance by operating the touch panel 2a (Si). The antiseptic solution is supplied to the monitoring device 1 belonging to a group that is frequently used for the treatment until a long time (for example, 60 minutes) elapses so as to perform the disinfecting. The antiseptic solution is supplied to the monitoring device 1 belonging to a group that is less frequently used for the treatment until a short time (for example, 30 minutes) elapses so as to perform the disinfecting (S2).

In this manner, a series of controls during the disinfecting is completed. By completing the above-described controls and sequentially performing the disinfecting on the monitoring device 1 of each group according to the treatment frequency, it is possible to efficiently perform the disinfecting. In the above-described embodiment, the disinfecting time is set according to the treatment frequency. However, instead of the treatment frequency, the disinfecting time may be set according to pipe capacity in the monitoring device 1.

According to the above-described embodiment, the predetermined information can be transmitted from the dialysate supplying device 2 to the specified monitoring device 1 out of the plurality of monitoring devices 1. The specified monitoring device 1 can perform the individual operation. Therefore, the monitoring devices 1 can perform the individual operation depending on various situations, such as power supply conditions and undiluted dialysate conditions. In addition, it is preferable to configure a control 11 such that in the monitoring device 1 to which the predetermined information is transmitted, operations are individually determined so as to further improve the operation.

Furthermore, according to the present embodiment, the supplying mechanism includes the dialysate supplying device 2 that produces the dialysate with the predetermined concentration by using the clean water and the undiluted dialysate. The blood purification mechanism includes the monitoring devices 1 that supply the dialysate supplied from the dialysate supplying device 2 to the dialyzer 5 (blood purifier). Therefore, the blood purification system can be applied to a central system. In addition, since the monitoring devices 1 and the dialysate supplying device 2 can bilaterally communicate with each other, various items of the information can be communicated between the monitoring devices 1 and dialysate supplying device 2. Thus, it is possible to perform a more appropriate blood purification treatment.

The blood purification system according to the present embodiment has been described, however, it is not intended to limit the present disclosure. For example, instead of those adapted to have the central system as described above, as illustrated in FIG. 8, the blood purification system may be applied to a system where the supplying mechanism includes the water treatment device 4, producing the clean water, and personal dialysis devices 20. The personal dialysis devices 20 produce the dialysate with the predetermined concentration, by using the clean water supplied from the water treatment device 4, and supply the dialysate to the dialyzer 5 (blood purifier). In this case, the personal dialysis devices 20 include tanks T1, respectively, containing the undiluted dialysate or the antiseptic solution. The tanks T1 are connected to the water treatment device 4 by a pipe L9. The personal dialysis devices 20 can produce the dialysate with the predetermined concentration by using the clean water supplied from the water treatment device 4 and the undiluted dialysate inside the tanks T1, or can produce the diluted antiseptic solution.

In the embodiment illustrated in FIG. 1, the supplying mechanism includes the dialysate supplying device 2, including the dissolving device 3 and the water treatment device 4, that supplies the dialysate to each of the monitoring devices 1. However, the blood purification system may be configured such that the blood purification mechanism has the dialyzer 5 (blood purifier) and the personal dialysis device 20 that can produce the dialysate from the undiluted dialysate inside the tanks T1.

Instead of those adapted to have the central system, as illustrated in FIG. 9, the blood purification system may be applied to a system where the supplying mechanism includes the water treatment device 4 and the dissolving device 3. The water treatment device 4 produces the cleaning water. The dissolving device 3 produces the undiluted dialysate with the predetermined concentration, by using the clean water produced by the water treatment device 4. The blood purification mechanism is adapted to have personal dialysis devices 21. The personal dialysis devices 21 produce the dialysate with the predetermined concentration by using the undiluted dialysate and the clean water, which are respectively supplied from the dissolving device 3 and the water treatment device 4. The personal dialysis devices supply the dialysate to the dialyzer 5 (blood purifier). In this case, the personal dialysis devices 21 include tanks T2 respectively containing the antiseptic solution. The tanks T2 are connected to the dissolving device 3 and the water treatment device 4 by pipes L10 and L11. The personal dialysis devices 21 can produce the dialysate with the predetermined concentration by using the undiluted dialysate and the clean water, which are respectively supplied from the dissolving device 3 and the water treatment device 4, or can produce the diluted antiseptic solution.

In the embodiment illustrated in FIG. 1, the supplying mechanism is configured to have the dialysate supplying device 2, including the dissolving device 3 and the water treatment device 4, that can supply the dialysate to each of the monitoring devices 1. However, the blood purification system may be configured such that the blood purification mechanism includes the dialyzer 5 (blood purifier) and the personal dialysis devices 21. The personal dialysis devices 21 produce the dialysate by using the undiluted dialysate and the clean water which are supplied from the supplying mechanism side.

In addition, in the present embodiment, the LAN connection is made to enable bilateral communication between the dialysate supplying device 2 and the monitoring devices 1. However, it is sufficient if the predetermined information can be transmitted from the dialysate supplying device 2 to the specified monitoring device 1 out of the plurality of monitoring devices 1 (blood purification mechanism). The specified monitoring device 1 can perform the individual operation. The predetermined information may be unilaterally transmitted from the dialysate supplying device 2 to the monitoring device 1. The present embodiment is applied to a system to perform the hemodialysis treatment, but may be applied to a blood purification system to perform a different blood purification treatment.

As long as a blood purification system is configured such that predetermined information can be transmitted from a supplying mechanism to a specified blood purification mechanism out of multiple blood purification mechanism and the specified blood purification mechanism can be caused to perform an individual operation, the blood purification system can be applied to those having other added functions.

The present disclosure has been described with reference to the preferred embodiment. Obviously, modifications and alternations will occur to those of ordinary skill in the art upon reading and understanding the preceding detailed description. It is intended that the present disclosure be construed to include all such alternations and modifications insofar as they come within the scope of the appended claims or their equivalents.

What is claimed is:

1. A blood purification system comprising:
multiple blood purification mechanisms, each including a blood purifier to perform blood purification treatment on a patient, the multiple blood purification mechanisms each comprise a control unit; and
supplying mechanism supplying a dialysate, an undiluted dialysate, clean water or an antiseptic solution to each of the blood purification mechanisms;
a specified control unit of a specified blood purification mechanism is programmed to receive predetermined information between the supplying mechanism and the specified blood purification mechanism, out of the multiple blood purification mechanisms, the specified blood purification mechanism control unit, based upon the information, is programmed so that the specified blood purification mechanism receives a specific amount of the dialysate, undiluted dialysate, clean water or antiseptic solution to perform an individual operation specific to the patient at the specified blood purification mechanism;
the specified control unit of the specified blood purification mechanism is programmed, depending on situations of the supplying mechanism, to control the specified blood purification mechanism so that the specified blood purification mechanism is operated or stopped, or a drive amount of an actuator, provided in the specified blood purification mechanism, is decreased, so that the specified blood purification mechanism control unit is programmed to deliver the specific amount of the dialysate, undiluted dialysate, clean water or antiseptic solution to the specific blood purification mechanism; and
under a condition where the supplying mechanism determines the dialysate or the undiluted dialysate to be insufficient, a drive amount of a pump in the specified blood purification mechanism is decreased to decrease the use amount of the dialysate in the specified blood purification mechanism.

2. The blood purification system according to claim 1, wherein the supplying mechanism includes a dialysate supplying device that may produce a dialysate with a predetermined concentration by using clean water and an undiluted dialysate; and
the blood purification mechanism includes a monitoring device that supplies the dialysate supplied from the dialysate supplying device to the blood purifier.

3. The blood purification system according to claim 1, wherein the supplying mechanism includes a water treatment device that may produce clean water; and
the blood purification mechanism includes a personal dialysis device that produces a dialysate with a predetermined concentration, by using the clean water supplied from the water treatment device, and supplies the dialysate to the blood purifier.

4. The blood purification system according to claim 1, wherein the supplying mechanism includes a water treatment device and a dissolving device, the water treatment device produces clean water and the dissolving device produces an undiluted dialysate with a predetermined concentration, by using the clean water produced in the water treatment device; and the blood purification mechanism includes a personal dialysis device that produces a dialysate with predetermined concentration by using the undiluted dialysate and the clean water that are respectively supplied from the dissolving device and the water treatment device, and supplies the dialysate to the blood purifier.

5. The blood purification system according to claim 1, wherein in a condition where insufficient electric power to be supplied to multiple blood purification mechanism is determined, a use amount of the electric power in the specified blood purification mechanism is decreased.

6. The blood purification system according to claim 1, wherein the specified blood purification mechanism includes a predetermined number of blood purification mechanisms that are divided into a group, out of the multiple blood purification mechanism.

7. The blood purification system according to claim 6, wherein disinfecting is sequentially performed for each group by supplying an antiseptic solution from the supplying mechanism to the specified blood purification mechanism that is divided into the group.

8. The blood purification system according to claim 1, wherein the specified blood purification mechanisms may be divided into a group depending on frequency of each blood purification treatment, and may be set to have disinfecting time according to a use frequency of the group.

9. The blood purification system according to claim 1, wherein the supplying mechanism and the blood purification mechanisms may bilaterally communicate with each other.

10. A blood purification system comprising:
multiple blood purification mechanisms, each including a blood purifier to perform blood purification treatment on a patient, the multiple blood purification mechanisms each comprise a control unit; and
supplying mechanism supplying a dialysate, an undiluted dialysate, clean water or an antiseptic solution to each of the blood purification mechanisms;
a specified control unit of a specified blood purification mechanism is programmed to receive predetermined information between the supplying mechanism and the specified blood purification mechanism, out of the multiple blood purification mechanisms, the specified blood purification mechanism control unit, based upon the information, is programmed so that the specified blood purification mechanism receives a specific amount of the dialysate, undiluted dialysate, clean water or antiseptic solution to perform an individual operation specific to the patient at the specified blood purification mechanism;
the specified control unit of the specified blood purification mechanism is programmed, depending on situations of the supplying mechanism, to control the specified blood purification mechanism so that the specified blood purification mechanism is operated or stopped, or a drive amount of an actuator, provided in the specified blood purification mechanism, is decreased, so that the specified blood purification mechanism control unit is programmed to deliver the specific amount of the dialysate, undiluted dialysate, clean water or antiseptic solution to the specific patient blood purification mechanism; and
under a condition where electric power to be supplied to multiple blood purification mechanisms is determined to be insufficient, a drive amount of a pump or heater in the specified blood purification mechanism is decreased to decrease the use amount of the electric power in the specified blood purification mechanism.

11. A blood purification system comprising:
multiple blood purification mechanisms, each including a blood purifier to perform blood purification treatment on a patient, the multiple blood purification mechanisms each comprise a control unit; and
supplying mechanism supplying a dialysate, an undiluted dialysate, clean water or an antiseptic solution to each of the blood purification mechanisms;
a specified control unit of a specified blood purification mechanism is programmed to receive predetermined information between the supplying mechanism and the specified blood purification mechanism, out of the multiple blood purification mechanisms, the specified blood purification mechanism control unit, based upon the information, is programmed so that the specified blood purification mechanism receives a specific amount of the dialysate, undiluted dialysate, clean water or antiseptic solution to perform an individual operation specific to the patient at the specified blood purification mechanism;
the specified control unit of the specified blood purification mechanism is programmed, depending on situations of the supplying mechanism, to control the specified blood purification mechanism so that the specified blood purification mechanism is operated or stopped, or a drive amount of an actuator, provided in the specified blood purification mechanism, is decreased, so that the specified blood purification mechanism control unit is programmed to deliver the specific amount of the dialysate, undiluted dialysate, clean water or antiseptic solution to the specific patient blood purification mechanism; and
under a condition where the supplying mechanism determines the dialysate or the undiluted dialysate to be insufficient, a drive amount of a pump in the specified blood purification mechanism is decreased to decrease the use amount of the dialysate in the specified blood purification mechanism; and
under a condition where electric power to be supplied to multiple blood purification mechanisms is determined to be insufficient, a drive amount of the pump or heater in the specified blood purification mechanism is decreased to decrease the use amount of the electric power in the specified blood purification mechanism.

* * * * *

UNITED STATES PATENT AND TRADEMARK OFFICE
CERTIFICATE OF CORRECTION

PATENT NO. : 10,220,131 B2
APPLICATION NO. : 14/093422
DATED : March 5, 2019
INVENTOR(S) : Masaru Kuchiki et al.

Page 1 of 1

It is certified that error appears in the above-identified patent and that said Letters Patent is hereby corrected as shown below:

In the Specification

Column 5
Line 15    "is" should be --1a--

Column 10
Line 62    "(Si)" should be --(S1)--

Signed and Sealed this
Fourth Day of June, 2019

Andrei Iancu
*Director of the United States Patent and Trademark Office*